United States Patent
Saito et al.

(12) 
(10) Patent No.: US 6,258,607 B1
(45) Date of Patent: Jul. 10, 2001

(54) INDIRECT AGGLUTINATION IMMUNOASSAY AND APPARATUS THEREFOR

(75) Inventors: Tomo Saito, Kawasaki; Mikio Ikeda, Tachikawa, both of (JP)

(73) Assignee: Fujirebio Inc., Tokyo (JP)

( * ) Notice: Subject to any disclaimer, the term of this patent is extended or adjusted under 35 U.S.C. 154(b) by 0 days.

(21) Appl. No.: 08/082,373

(22) Filed: Jun. 28, 1993

Related U.S. Application Data

(63) Continuation-in-part of application No. 07/606,205, filed on Oct. 31, 1990, now abandoned.

(30) Foreign Application Priority Data

Oct. 31, 1989 (JP) .................................................. 1-281895
Dec. 21, 1989 (JP) .................................................. 1-329556

(51) Int. Cl.⁷ ..................... G01N 33/553; G01N 33/555; G01N 33/551; G01N 33/552
(52) U.S. Cl. ......................... 436/526; 436/520; 436/524; 436/525; 436/531; 436/533; 436/534; 436/527; 436/806; 210/222; 422/68.1
(58) Field of Search ..................... 436/520, 526, 436/524, 525, 531, 533, 534, 527, 806; 210/222; 422/68.1

(56) References Cited

U.S. PATENT DOCUMENTS

| | | | |
|---|---|---|---|
| 4,148,607 | 4/1979 | Bernoco et al. | 436/520 X |
| 4,438,068 | 3/1984 | Forrest | 422/61 |
| 4,628,037 | * 12/1986 | Chagnon et al. | 436/526 |
| 4,770,855 | 9/1988 | Sakuma | 422/102 |

FOREIGN PATENT DOCUMENTS

| | | | |
|---|---|---|---|
| 0 030 087 | 6/1981 | (EP) . | |
| 0 351 857 | 10/1988 | (EP) . | |
| 0426170 | * 5/1991 | (EP) . | |
| 59-195161 | * 11/1984 | (JP) | 436/526 |
| 3173093 | * 12/1992 | (JP) | 436/526 |

OTHER PUBLICATIONS

Production and Use of Magnetiziable Particles in Immunoassay, M. Pourfarzaneh, Ph.D., et al., The Ligand Quarterly, vol. 5, No. 1, 1982, pp. 41–47.
Davis et al., "Microbiology", 2nd Edition, Harper & Row Publishers, Inc., Hagerstown, MD, p. 393, (1973).*

* cited by examiner

*Primary Examiner*—James Housel
*Assistant Examiner*—Brett Nelson
(74) *Attorney, Agent, or Firm*—Oblon, Spivak, McClelland, Maier & Neustadt, P.C.

(57) ABSTRACT

An indirect agglutination immunoassay includes the steps of providing, in a container, an immunoassay system comprising a test sample containing a desired analyte, and a reagent composed of magnetic particles or magnetic-material containing particles containing iron therein, wherein the magnetic particles or magnetic-material containing particles have been sensitized to allow specific binding to the desired analyte, and have a particle size in the range of 1 to 5 $\mu$m, with the content of the iron being in the range of 8 to 20 wt. %, precipitating the magnetic particles or magnetic-material containing particles by the application of magnetic force, allowing the container to stand at an inclination, and detecting the presence or absence of an immune reaction from the absence or presence of slippage observed of the precipitated magnetic particles or magnetic-material containing particles on the bottom of the container. An apparatus for conducting this indirect agglutination immunoassay is composed of the above container, a magnetic sedimentation device for magnetically precipitating the components containing the magnetic particles at the bottom of the container, and an inclination device for allowing the container to stand at an inclination after removal of the magnetic sedimentation device.

12 Claims, 11 Drawing Sheets

|  | <16 | 16 | 32 | 64 | 128 | 256 | 512 | 1024 | 2048 | 4096 | 8192 | >8192 |
|---|---|---|---|---|---|---|---|---|---|---|---|---|
| >8192 |  |  |  |  |  |  |  |  |  |  |  | 2 |
| 8192 |  |  |  |  |  |  |  |  |  |  | 1 |  |
| 4096 |  |  |  |  |  |  |  |  |  | 2 | 1 |  |
| 2048 |  |  |  |  |  |  |  |  | 1 | 3 |  |  |
| 1024 |  |  |  |  |  |  |  | 6 | 1 |  |  |  |
| 512 |  |  |  |  |  |  | 1 | 12 | 1 |  |  |  |
| 256 |  |  |  |  |  | 1 | 9 | 2 |  |  |  |  |
| 128 |  |  |  |  | 7 | 2 |  |  |  |  |  |  |
| 64 |  |  |  | 1 | 11 | 1 |  |  |  |  |  |  |
| 32 |  |  | 13 | 3 |  |  |  |  |  |  |  |  |
| 16 |  | 1 | 18 | 3 |  |  |  |  |  |  |  |  |
| <16 | 197 | 3 |  |  |  |  |  |  |  |  |  |  |

TITER — CONVENTIONAL METHOD (vertical axis)

TITER — INDIRECT AGGLUTINATION IMMUNOASSAY OF THE PRESENT INVENTION (horizontal axis)

1.9 μm : NORMAL SLIPPAGE 0.8 μm : SELF AGGREGATION 1.9 μm : PATTERN LENGTH 2.85 mm

3 μm : PATTERN LENGTH 2.35 mm l# INDIRECT AGGLUTINATION IMMUNOASSAY AND APPARATUS THEREFOR

This application is a continuation-in-part of application Ser. No. 07/606,205, filed Oct. 31, 1990, now abandoned.

BACKGROUND OF THE INVENTION

1. Filed of the Invention

The present invention relates to an indirect agglutination immunoassay and an apparatus therefor, and more particularly to an indirect agglutination immunoassay using an antigen-antibody reaction and magnetic particles or magnetic-material-containing particles, and an apparatus for conducting the indirect agglutination immunoassay.

2. Discussion of Background

Indirect agglutination used in an immunoassay, in which the combining reaction by the antigen-antibody reaction is intensified by use of antigen- or antibody-bonded particles, is called "passive agglutination" or "reverse passive agglutination" and is widely used in practice in a simple immunoassay for a large number of test samples.

The immunoassay utilizing indirect agglutination has the advantages over the conventional EIA (enzyme immunoassay) and RIA (radioimmunoassay) in that the assay is simple in operation and does not require any particular device for detecting the occurrence of the antigen-antibody reaction. However the immunoassay utilizing indirect agglutination has the drawbacks that it is extremely difficult to conduct the assay automatically, and it has not as yet been developed beyond the semi-automation stage.

There are two methods for forming detection patterns during indirect agglutination.

In one method, a particle-containing reagent is added to a diluted solution of a test sample containing a desired analyte placed in a "U" well or "V" well microplate, the mixture is stirred and then allowed to stand, and the occurrence of an antigen-antibody reaction is detected from a sedimentation pattern of the particles of the reagent formed at the bottom of the well. Hereinafter this method is referred to as "the standing method".

In another method, a particle-containing reagent is added to a diluted solution of the test sample placed in a "U" well or "V" well microplate, and the mixture is stirred and then centrifuged to precipitate the particles onto the bottom of the well. The microplate is then inclined, so that the presence or absence of an antigen-antibody reaction is detected from the absence or presence of slippage observed of a coating of the precipitated particles at the bottom of the well of the microplate. Hereinafter this method is referred to as "the centrifugation method".

In the case where the occurrence of an antigen-antibody reaction is detected from the sedimentation pattern by the standing method, it is extremely difficult to detect the pattern automatically because the pattern is easily distorted by slight vibrations during the standing thereof. As a result, for instance, the pattern is deformed, the area of the pattern is decreased, and slippage of the pattern along the bottom of the well takes place. In addition, the standing method has the drawback that about 0.5 to 3 hours are required before the pattern is formed in a suitable fashion for the assay, although the necessary time period for this of course depends upon the type of particles employed.

In contrast, in the case of the centrifugation method, the sedimentation can be finished within a few minutes by use of a centrifuge, and the pattern can be read after the microplate is slanted for several minutes. Furthermore, the concern about the distortion of the pattern caused by vibrations applied thereto during the formation of the pattern is entirely unnecessary. However, it is difficult to perform the immunoassay automatically by use of a centrifuge in practice.

As test samples that can be used for the above-mentioned conventional standing method and centrifugation method, for instance, blood serum, urine, and other body fluids can be given. In conventional methods, the test samples are usually diluted and used. However, when whole blood is used without separating out of the blood corpuscles and blood serum, the sedimentation pattern tends to be centered at one point of the bottom of the well of the microplate, so that the blood components adversely affect the shape of the agglutination or sedimentation pattern. It is known that this will distort the results of the assay.

In other conventional immunoassays, such as the EIA (enzyme immunoassay) and RIA (radioimmunoassay), the separation of blood corpuscles and blood serum is conducted as a pre-processing step in order to avoid non-specific reactions.

SUMMARY OF THE INVENTION

It is therefore a first object of the present invention to provide a simplified, automatic indirect agglutination immunoassay with an increased magnetic sedimentation rate.

A second object of the present invention is to provide an apparatus for performing the above agglutination immunoassay automatically.

According to the present invention, the first object of the present invention can be achieved by an indirect agglutination immunoassay comprising the steps of:

providing, in a container, an immunoassay system comprising a test sample containing a desired analyte, and a reagent comprising magnetic particles or magnetic-material containing particles containing iron, wherein the magnetic particles or magnetic-material containing particles have been sensitized to allow specific binding to the desired analyte, and have a particle size in the range of 1 to 5 $\mu$m, with the content of the iron being in the range of 8 to 20 wt. %, precipitating the magnetic particles or magnetic-material containing particles by the application of magnetic force, allowing the container to stand at an inclination, and detecting the presence or absence of an immune reaction from the absence or presence of slippage observed of the precipitated magnetic particles or magnetic-material containing particles on the bottom of the container.

In the above magnetic agglutination immunoassay, the magnetic particles can be precipitated by use of either an electromagnet or a permanent magnet.

The second object of the present invention can be achieved by an apparatus for conducting an indirect agglutination immunoassay comprising (a) a container which contains a test sample for immunoassay, and sensitized magnetic particles or sensitized magnetic-material containing particles, having a particle size in the range of 1 to 5 $\mu$m, which contain iron in an amount in the range of 8 to 20 wt. %, (b) a magnetic sedimentation means for magnetically precipitating the components containing the magnetic particles at the bottom of the container, and (c) an inclination means for allowing the container to stand at an inclination after removal of the magnetic sedimentation means.

BRIEF DESCRIPTION OF THE DRAWINGS

A more complete application of the invention and many of the attendant thereof will be readily obtained as the same becomes better understood by reference to the following detailed description when considered in connection with the accompanying drawings, wherein:

FIG. 4 to 6 are the diagrams showing the relationship between the immunoassay according to the present invention and a conventional standing method with respect to the respective titers;

DETAILED DESCRIPTION OF THE PREFERRED EMBODIMENTS

In the present invention, the magnetic particles or magnetic-material containing particles, each containing iron, are sedimented by the magnetic force of a magnet to the bottom of each well of a well microplate which is placed on a magnetic sedimentation acceleration base.

When a well microplate with wells, each well having a V-shaped bottom (hereinafter referred to as a V-shaped well microplate), is employed, the magnetic sedimentation acceleration base performs the same function of sedimenting the magnetic particles by force as a centrifuge does, so that the time required for an immunoassay can be reduced to ⅓ or less of the time required for the conventional standing method. Furthermore, the assay is completely unaffected by vibrations.

Furthermore, when the V-shaped well microplate is employed, the magnetic particles are collected substantially in the same shape at the bottom of each well, regardless of the shape of the magnet employed for the magnetic sedimentation. In contrast, when a U-shaped or flat-bottom well microplate, with the bottom of each well being U-shaped or flat, is employed, however, the shape of the employed magnet has a decisive effect on the shape or pattern of the sedimented magnetic particles at the bottom of each well. In other words, if it is desired to sediment the magnetic particles in the shape of a spot on the bottom of each of the U-shaped or flat-shaped well, it is preferable that the magnet have a tip which is situated close to or in contact with the external lower bottom of each well. If the magnet has a rectangular end which is situated close to or in contact with the external lower bottom of each well, the magnetic particles are sedimented in the bottom of each well, in such a shape as to correspond to the shape of the rectangular end of the magnet.

Figure 7:
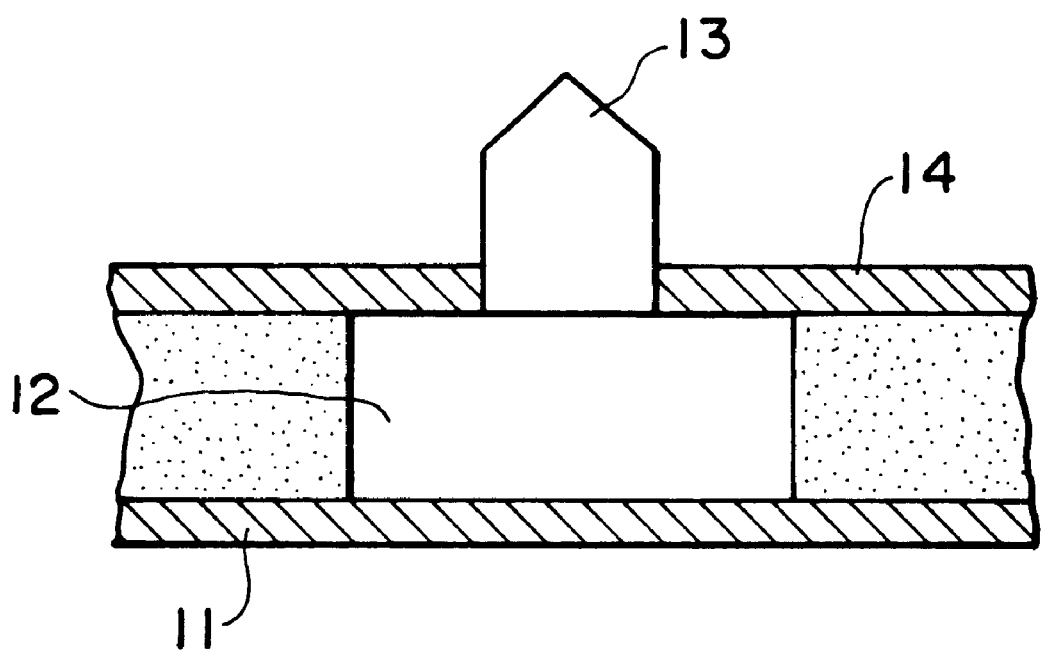
FIG. 7 is a schematic cross-sectional view of a magnet with a steel adaptor.

In order to attain the spot-shaped sedimentation of the magnetic particles in the bottom of the U-shaped or flat well, instead of using a magnet with a pointed tip, a pointed shaped adaptor made of steel can be attached to any types of a magnet as illustrated in FIG. 7.

In FIG. 7, reference numeral 11 indicates a support, and reference numeral 12 indicates a magnet which is placed on the support. Reference numeral 13 indicates an adaptor which is made of steel and in contact with the magnet 12. Reference numeral 14 indicates a non-magnetic holding member which is made of a non-magnetic or magnetic-force-shielding material, such as plastics. The magnet 12 is held between the support 11 and the non-magnetic holding member 14, if necessary with a spacer (not shown) between the support 11 and the non-magnetic holding member 14, and the adaptor 13 is projected through the non-magnetic holding member 14 as illustrated in FIG. 7 and the tip of the adaptor 13 is situated in close to or in contact with the external bottom of each well of the U-shaped or flat-bottom well microplate.

For the practical use of the adaptor 13 as shown in FIG. 7, the same number of the adaptors 13 as that of the wells of the U-shaped or flat-bottom well microplate is provided on a magnetic attraction base in such a configuration that the tip of each adaptor 13 is positioned close to or in contact with the external bottom of each well.

Figure 8:
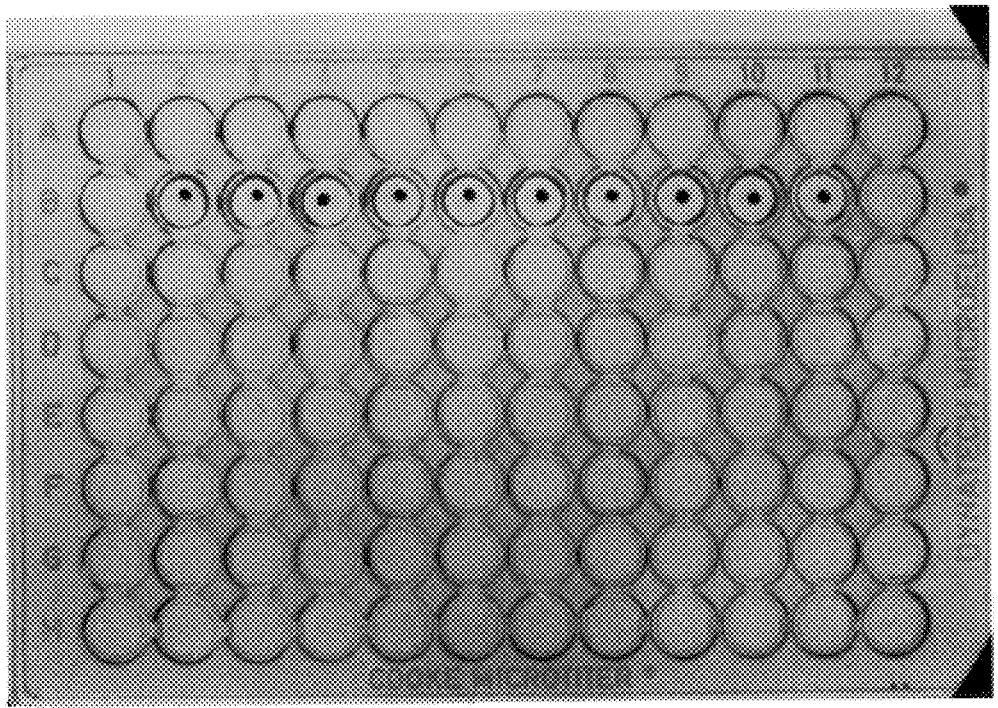
FIG. 8 shows an example of a sedimentation pattern of magnetic particles in each of the flat bottom wells of a flat well microplate immediately after magnetic sedimentation by use of a magnetic attraction base including an adaptor.

FIG. 8 shows an example of the sedimentation pattern of the magnetic particles in each of the flat bottom wells of a flat-bottom well microplate immediately after the magnetic sedimentation by use of the above-mentioned magnetic attraction base including the adaptors 13.

Figure 9:
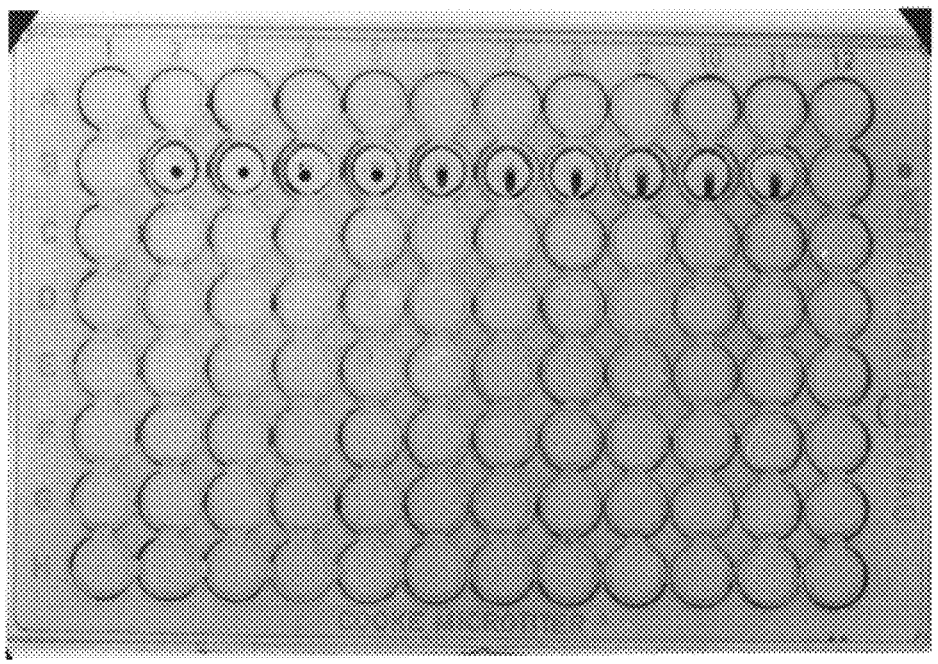
FIG. 9 shows a sedimentation pattern of magnetic particles in each of the flat bottom wells of a flat bottom well microplate at the inclination thereof.
Figure 10:
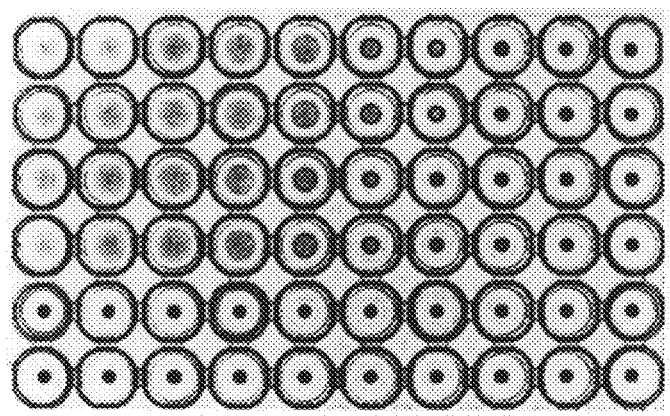
FIGS. 10 to 13 show sedimetnation patterns obtained in Example 13.
Figure 11:
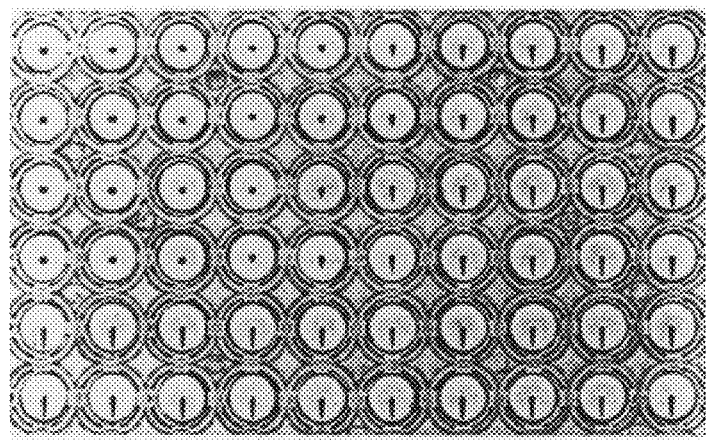
Figure 12:
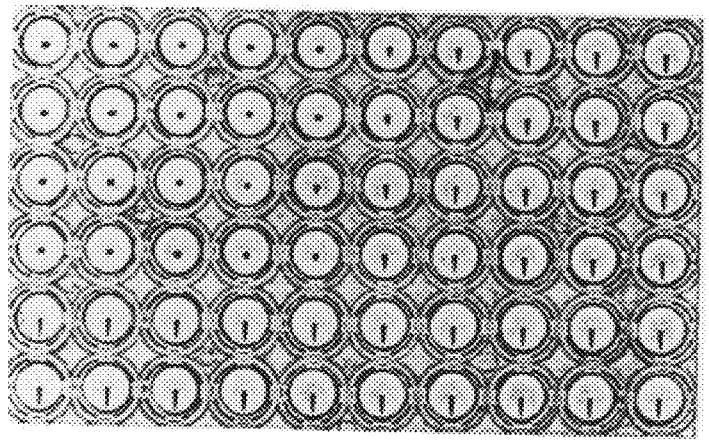
Figure 13:
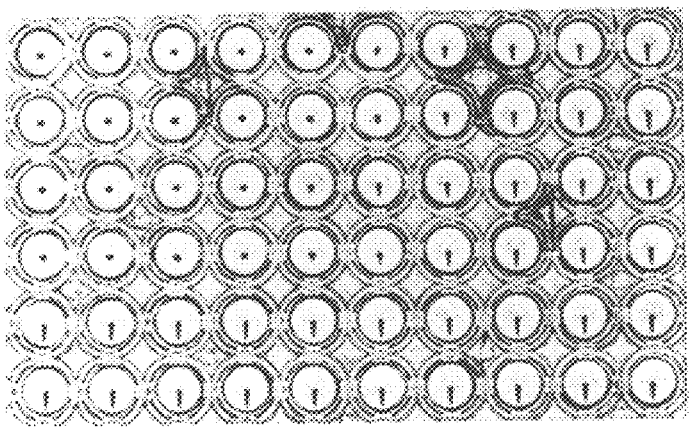

FIG. 9 shows the sedimentation pattern of the magnetic particles in each of the flat-bottom wells of a flat well microplate when the flat well microplate was inclined.

The above-mentioned flat-bottom well microplate can be used only in combination with magnetic particles, which can be attracted by magnetic force. The flat-bottom well microplate has the advantage that the distance between each pattern of the sedimented magnetic particles and a pattern reader or sensor can be made constant.

Figure 1:
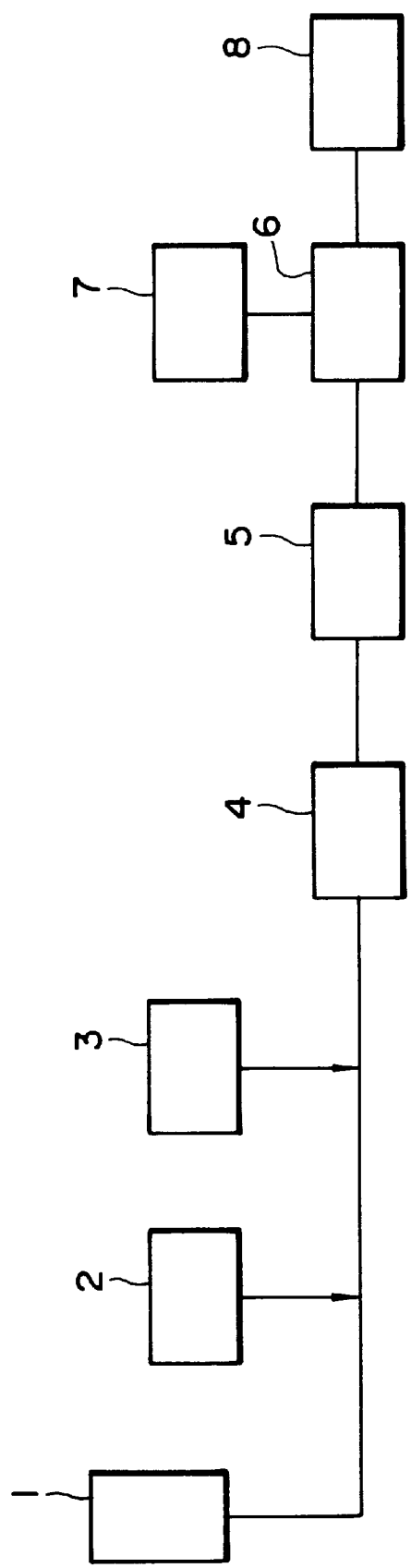
FIG. 1 is a block diagram of an apparatus for conducting the indirect agglutination immunoassay according to the present invention.

In sharp contrast to this, when the V-shaped bottom well microplate is employed, and the length of each slippage pattern of the magnetic particles is measured by use of the pattern read apparatus 7 as shown in FIG. 1, the accuracy of the alignment of the wells, in particular, the accuracy of the alignment of the centers of the wells, is extremely important to obtain reliable data for the length of each slippage pattern with high reproducibility, because if the alignment of the centers of the wells is not accurate, reliable data cannot be obtained by the pattern read apparatus 7 as shown in FIG. 1. Furthermore, since the V-shaped bottom well microplates are mass produced, it is difficult to produce them with high accuracy of the alignment of the centers of the wells.

However, in the case of the magnetic attraction base provided with the adaptors 13, however, it is not difficult to control the position of each adaptor 13 with high accuracy in the magnetic attraction base.

Thus, the flat bottom well microplate has the advantage that more reliable data can be obtained with high reproducibility can be obtained over V-shaped bottom well microplate.

The magnetic particles or magnetic-material containing particles to be contained in the reagent for use in the present invention have a particle size in the range of 1 μm to 5 μm, preferably in the range of 1.5 μm to 3.0 μm, and each contains iron in an amount in the range of 8 to 20 wt. %.

Examples of such magnetic particles or magnetic-material containing particles include magnetic particles, ferrimagnetic-material containing gelatin particles, magnetic particles comprising a magnetic material coated with blood serum alubmin or a polymeric material, and magnetic-material containing polymer particles.

In the above magnetic particles or magnetic-material containing particles (hereinafter referred to as the magnetic particles), the percentage of the content of the iron is measured as follows:

The magnetic particles, such as ferrimagnetic-material containing gelatin particles, are centrifuged at 12,500 G (10,000 rpm) for 10 minutes, and the weight of the resultant particles is measured, with the elimination of a supernatant liquid, if any. The thus measured weight is referred to weight A, which is also referred to as the wet weight of the magnetic particles.

The amount of the iron contained in the magnetic particles, which is referred to as weight B, is measured by a conventional method, so that the percentage of the iron is calculated by the following formulas:

(Weight B/Weight A)×100%=Percentage of Iron Content

Test samples that can be tested by the magnetic agglutination immunoassay according to the present invention include blood serum, urine, body fluid, and whole blood. When whole blood is tested, only the components which contain the magnetic particles or magnetic-material containing particles are sedimented by magnetic force at the bottom of the well. Therefore, the blood corpuscle components in the test sample spread throughout the test sample in the well, and only the components which contain the magnetic particles or magnetic-material containing particles are selectively sedimented at one portion of the bottom of the well. Therefore even if whole blood is employed, the pattern formed by the components which contain the magnetic particles or magnetic-material-containing particles is not substantially affected by other components present in the test sample, and if any, the affect is in fact negligible.

When the well is colored red in its entirety by the blood corpuscle components and it is difficult to observe the sedimentation, the observation can be done easily by covering the well with a red-colored filter, made of, for example, glass, plastic film or cellophane.

As the wells for the test samples and reagents for use in the present invention, V-shaped, U-shaped, or flat-bottom, large or small, wells made of a plastic resin, such as polystyrene resin, ABS resin, or glass, can be employed.

In order to test a large number of test samples, it is preferable to use V-shaped well microplates made of polystyrene because the formed patterns can be clearly observed.

As mentioned previously, the flat-bottom well microplate can also be employed. When the length of a slippage pattern of the magnetic particles is measured by use of the flat-bottom well microplate, the shape of the leading edge of the slippage pattern can be changed so that the slippage pattern does not have a sharp leading edge, such as to a spindle-shaped slippage pattern, by changing the shape of a portion of a magnet or of the previously mentioned adaptor 13, which comes into contact with the external bottom of each well of the flat-bottom well microplate. Thus, the reproducibility of the measurement of the length of slippage pattern can be improved.

As mentioned previously, the apparatus for conducting the magnetic agglutination immunoassay according to the present invention comprises (a) a container such as any of the above-mentioned wells which contains a test sample for immunoassay, and sensitized magnetic particles or sensitized magnetic-material containing particles, having a particle size in the range of 1 to 5 μm, which contain iron in an amount in the range of 8 to 20 wt. %, (b) a magnetic sedimentation means for magnetically precipitating the components containing the magnetic particles at the bottom of the container, and (c) an inclination means for allowing the container to stand at an inclination after removal of the magnetic sedimentation means.

An example of the apparatus according to the present invention, which is automized for use in practice, will now be explained with reference to FIG. 1, which is a diagram of the apparatus and is given for illustration of the invention and is not intended to be limiting thereof.

In FIG. 1, reference numeral 1 indicates a microplate supply device comprising, for instance, a number of V-shaped wells on a microplate (not shown), which serve as the above-mentioned well for holding a test sample for immunoassay, and magnetic particles which can accept a reagent for immunoassay; reference numeral 2, a test sample supply device for supplying a test sample; reference numeral 3, a reagent supply device for supplying a reagent comprising magnetic particles or magnetic-material containing particles; reference numeral 4, a stirrer for stirring the test sample and the reagent; reference numeral 5, a sedimentation acceleration device for sedimenting the magnetic particles or magnetic-material-containing particles at the bottom of the microplate; reference numeral 6, an inclination device for allowing the microplate supply device 1 to stand at an inclination; reference numeral 7, a pattern read apparatus for reading or detecting the slippage state of the sedimented particles on the bottom caused by the inclination of the microplate supply device 1; and reference numeral 8, a microplate recovery device for recovering the used microplates.

As mentioned previously, in the present invention, magnetic particles with a particle size of 1 μm to 5 μm, preferably a particle size in the range of 1.5 μm to 3.0 μm, are selectively used. This is because when the magnetic particles with the particle size in the above-mentioned range, the presence or absence of an immune reaction can be most accurately detected.

In order to demonstrate this, the following tests were carried out:

REFERENCE EXAMPLE 1

Preparation of Gelatin Particle Containing Anti-human Hemoglobin (Hb) Sensitized Ferricolloid Ferricolloid-containing gelatin particles were washed with a 50% ethanol three times, and were then further washed with saline 3 times. Thereafter, these particles were immersed in a 0.15 M phosphate buffered saline (PBS) (pH 6) containing an anti-human hemoglobin (Hb) at room temperature for 2 hours. The particles were then washed with saline three times and were dispersed in a 0.14 M phosphate buffered saline (pH 7.0) containing 0.2% bovine serum albumine, whereby gelatine particle containing anti-human Hemoglobin (Hb) sensitized ferricolloid, with a particle size of 1.9 μm, and the content of iron being 12 wt. %, was prepared.

In the same manner as mentioned above, first comparative gelatin particles containing anti-human Hemoglobin (Hb) sensitized ferricolloid, with a particle size of 0.8 μm, and the content of iron being 12 wt. %, was also prepared.

Furthermore, in the same manner as mentioned above, second comparative gelatin particles containing anti-human Hemoglobin (Hb) sensitized ferricolloid, with a particle size of 3.0 μm, and the content of iron being 12 wt. %, was also prepared.

REFERENCE EXAMPLE 2

Fecal Occualt Blood Test

50 μl of a standard Hemoglobin test sample was placed in a first V-shaped well of a microplate. 25 μl of a dilution liquid was placed in each of a second well through an eighth well of the microplate. 25 μl of the diluted Hemoglobin test sample was taken from the first well, and by use of the diluted Hemoglobin test sample, a $2^n$ dilution was sequentially performed from the second well through the eighth well. To each diluted test sample placed in the V-shaped wells of the microplate was added 25 μl of a dispersion of the gelatin particles containing anti-human Hemoglobin sensitized ferricolloid prepared in Reference Example 1 at a concentration of 0.1%.

Figure 14:
FIGS. 14 and 15 show the comparsion in the slippage of sedimented, aggultinated magentic marticles with respect to the particle sizes thereof.

The mixture was stirred for 3 minutes. The microplate was allowed to stand on a magnet-including sedimentation acceleration base for 3 minutes. The microplate was then removed from the sedimentation acceleration base and placed on a pattern reading base free from the effect of magnetic force and allowed to stand thereon at an inclination of about 60° for one minute to inspect the slippage state of a coating of the sedimented particles on the bottom of each well, whereby the presence or absence of the immune reaction was detected. FIG. 14 shows the slippage state which was found appropriate in comparison with other conventional dection methods.

The above-mentioned procedure was repeated except that the gelatine particle containing anti-human Hemoglobin (Hb) sensitized ferricolloid, with a particle size of 1.9 μm, and the content of iron being 12 wt. % employed in the above was replaced by the first comparative gelatin particles containing anti-human Hemoglobin (Hb) sensitized ferricolloid, with a particle size of 0.8 μm, and the content of iron being 12 wt. %, prepared in Reference Example 1, whereby the slippage of the precipitated magnetic particles on the bottom of the well inspected.

As indicated in FIG. 14, the slippage was too short to be determined to be negative with respect to the immune reaction because of the self aggregation of the magnetic particles when the diameter of the magnetic particles was 0.8 μm, in comparison with the slippage observed in the case where the diameter of the magnetic particles was 1.9 μm.

The above-mentioned procedure was repeated except that the gelatine particle containing anti-human Hemoglobin (Hb) sensitized ferricolloid, with a particle size of 1.9 μm, and the content of iron being 12 wt. % employed in the above was replaced by the second comparative gelatin particles containing anti-human Hemoglobin (Hb) sensitized ferricolloid, with a particle size of 3.0 μm, and the content of iron being 12 wt. %, prepared in Reference Example 1, whereby the slippage of the precipitated magnetic particles on the bottom of the well inspected.

Figure 15:
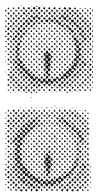

As indicated in FIG. 15, the slippage was rather short to be determined to be negative with respect to the immune reaction when the diameter of the magnetic particles was 3.0 μm, in comparison with the slippage observed in the case where the diameter of the magnetic particles was 1.9 μm.

EXAMPLE 1

Preparation of Gelatin Particles Containing Anti-human Alpha(α)-fetoprotein (AFP) Sensitized Ferricolloid Gelatin particles containing anti-human AFP sensitized ferricolloid were prepared by the application of anti-human AFP antibody (rabbit, DACO) to ferricolloid-containing gelatin particles having an average particle size of about 3 microns disclosed in Japanese Laid-Open Patent Application 59-195161 in accordance with a method by Barnard et al. (Clin. Chem., 27 (6) 832 (1981)).

EXAMPLE 2

Assay of AFP in Blood Serum

Each of a series of blood serum test samples containing AFP at a different concentration was diluted by 10 times with a blood serum dilution liquid.

Each of the thus diluted blood serum test samples was placed in the V-shaped wells of a microplate. To each diluted test sample placed in the V-shaped well of the microplate was added 25 μl of a dispersion of the gelatin particles containing anti-human AFP sensitized ferricolloid prepared in Example 1 with a concentration of 0.09%. The mixture was stirred for 10 minutes.

Figure 3:
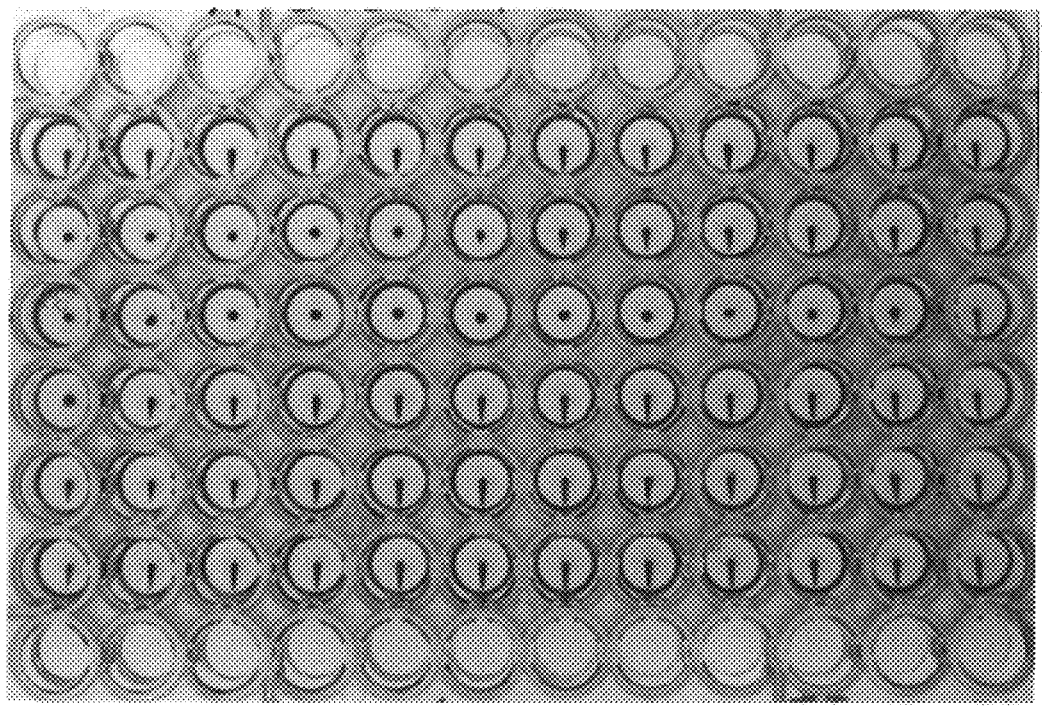
FIG. 3 is a view of an example of the observation of test samples by use of a V-shaped well microplate.

The microplate was allowed to stand on a magnet-including sedimentation acceleration base for 5 minutes. The microplate was then removed from the sedimentation acceleration base and placed on a pattern reading base free from magnetic force and allowed to stand thereon at an inclination of about 70° for one minute to observe the slippage state of a coating of the sedimented particles at the bottom of each well, whereby the presence or absence of the immune reaction was judged. When slippage was observed in the coating of the sedimented particles, the immune reaction was judged not to have occurred, that is, the immune reaction was negative, while when no slippage of the coating of the sedimented particles was observed, the immune reaction was judged to have occurred, that is, the immune reaction was positive. FIG. 3 shows a view of an example of an observation of an example of such test samples obtained by use of a V-shaped well microplate.

Figure 2:
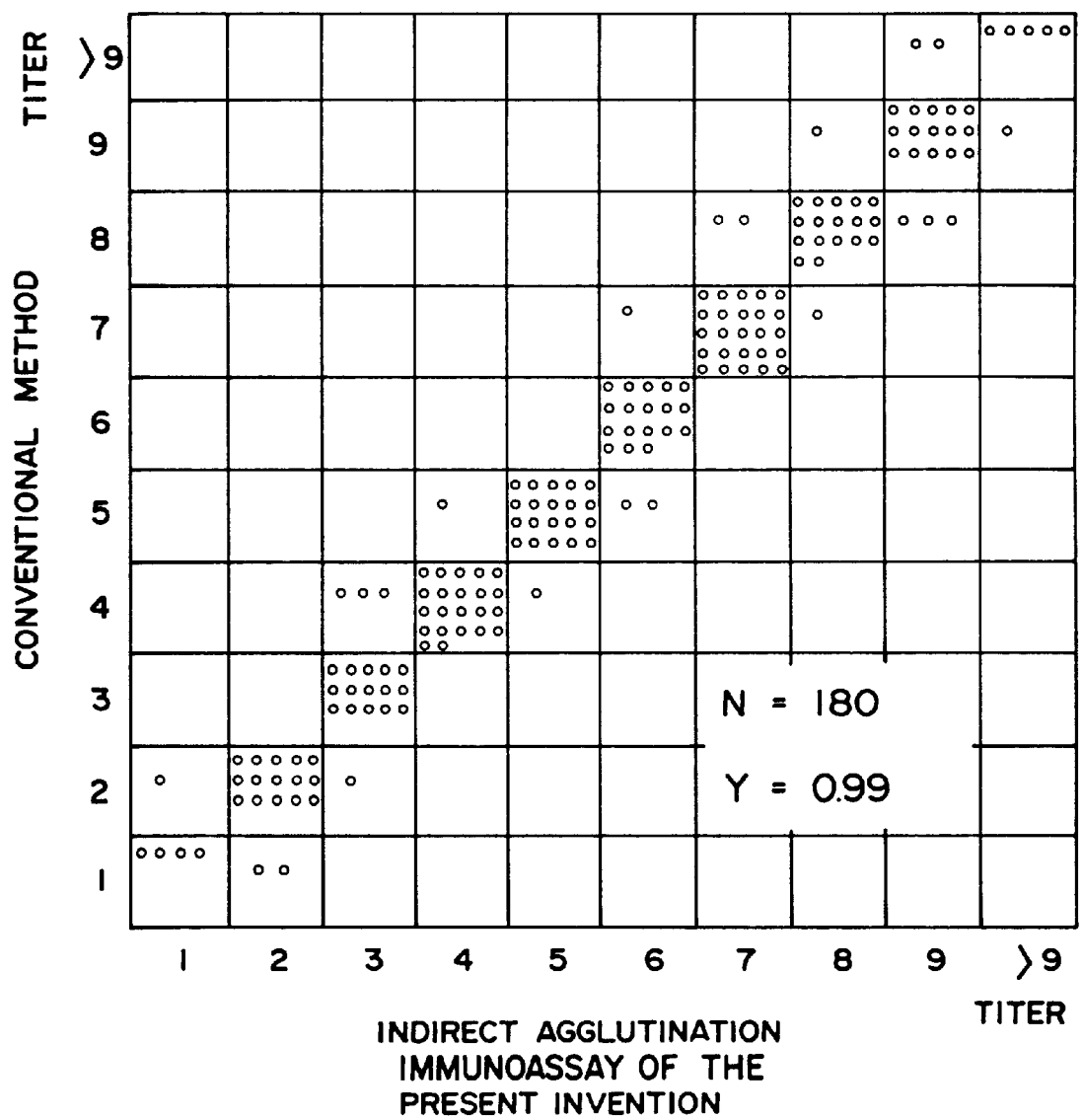
FIG. 2 is a diagram showing the relationship between the immunoassay according to the present invention and a conventional standing method with respect to the respective titers.

FIG. 2 shows the relationship between the above-mentioned immunoassay according to the present invention and a conventional standing method using a commercially available reagent for the assay of alpha(α)-fetoprotein (Trademark "Serodia AFP mono" made by Fujirebio Inc.) with respect to the respective titers.

EXAMPLE 3

Assay of AFP in Blood Serum

A blood serum test sample containing AFP was diluted by 10 times with a blood serum dilution liquid. 50 μl of the thus diluted blood serum test sample was placed in a first V-shaped well of a microplate. 25 μl of the blood serum dilution liquid was placed in each of a second well through an eighth well of the microplate. 25 μl of the diluted blood serum test sample was taken from the first well, and by use of the diluted blood serum test sample, a $2^n$ dilution was sequentially performed from the second well through the eighth well. To each diluted test sample placed in the V-shaped wells of the microplate was added 25 μl of a dispersion of the gelatin particles containing anti-human AFP sensitized ferricolloid prepared in Example 1 at a concentration of 0.14%. The mixture was stirred for 3 minutes. The microplate was allowed to stand on a magnet-including sedimentation acceleration base for 3 minutes. The microplate was then removed from the sedimentation acceleration base and placed on a pattern reading base free from the effect of magnetic force and allowed to stand thereon at an inclination of about 45° for one minute to observe the slippage state of a coating of the sedimented particles on the bottom of each well, whereby the presence or absence of the immune reaction was judged in the same manner as in Example 2. The results are shown in TABLE 1.

EXAMPLE 4

Assay of AFP in Whole Blood

A blood serum test sample containing AFP was diluted by 5 times with a blood serum dilution liquid. To this diluted blood serum test sample was added a whole blood collected from a man in good health in an amount equal to the amount of the diluted blood serum test sample, whereby a test sample was prepared.

50 μl of the thus prepared test sample was placed in a first V-shaped well of a microplate. 25 μl of the blood serum dilution liquid was placed in each of a second well through an eighth well of the microplate. 25 μl of the test sample was taken from the first well, and by use of the diluted test sample, a $2_n$ dilution was sequentially performed from the second well through the eighth well. To each diluted test sample placed in the V-shaped wells of the microplate was added 25 μl of a dispersion of the gelatin particles containing anti-human AFP sensitized ferricolloid prepared in Example 1 at a concentration of 0.14%. The mixture was stirred for 3 minutes.

The microplate was allowed to stand on a magnet-including sedimentation acceleration base for 3 minutes. The microplate was then removed from the sedimentation acceleration base and placed on a pattern reading base free from the effect of magnetic force and allowed to stand thereon at an inclination of about 45° for one minute to observe the slippage state of a carpet of the sedimented particles from the bottom of each well, whereby the presence or absence of the immune reaction was judged. The results are shown in TABLE 1.

TABLE 1

| | Example 4 | | |
|---|---|---|---|
| Final Dilution Ratio (Blood Serum) | Example 3 Judgement | Final Dilution Ratio (Whole Blood) | Judgement |
| 1:20 | + | 1:4 | +* |
| 1:40 | + | 1:8 | +* |
| 1:80 | + | 1:16 | + |
| 1:160 | + | 1:32 | + |
| 1:320 | − | 1:64 | − |
| 1:640 | − | 1:128 | − |
| 1:1280 | − | 1:256 | − |
| 1:2560 | − | 1:512 | − |

+: Positive
−: Negative
*: Difficult to judge

EXAMPLE 5

Assay of AFP in Blood Serum

Each of a series of blood serum test samples containing AFP at a different concentration was diluted by 10 times with a blood serum dilution liquid.

Each of the thus diluted blood serum test samples was placed in the V-shaped wells of a microplate. To each diluted test sample placed in the V-shaped well of the microplate was added 25 μl of a dispersion of the gelatin particles containing anti-human AFP sensitized ferricolloid prepared in Example 1 at a concentration of 0.14%. The mixture was stirred for 5 minutes.

The microplate was allowed to stand on a magnet-including sedimentation acceleration base for 5 minutes. The microplate was then removed from the sedimentation acceleration base and placed on a pattern reading base free from the effect of magnetic force and allowed to stand thereon at an inclination of about 45° to observe the slippage state of a coating of the sedimented particles at the bottom of each well. One minute later, the presence or absence of the immune reaction was judged. As mentioned previously when slippage was observed in the coating of the sedimented particles, the immune reaction was judged not to have occurred, that is, the immune reaction was negative, while when no slippage of the coating of the sedimented particles was observed, the immune reaction was judged to have occurred, that is, the immune reaction was positive.

EXAMPLE 6

Assay of AFP in Blood Serum

A blood serum test sample containing AFP was diluted by 10 times with a blood serum dilution liquid. 50 μl of the thus diluted blood serum test sample was placed in a first V-shaped well of a microplate. 25 μl of the blood serum dilution liquid was placed in each of a second well through an eighth well of the microplate. 25 μl of the diluted blood serum test sample was taken from the first well, and by use of the diluted blood serum test sample, a $2^n$ dilution was sequentially performed from the second well through the eighth well.

To each diluted test sample placed in the V-shaped wells of the microplate was added 25 μl of a dispersion of the gelatin particles containing anti-human AFP sensitized ferricolloid prepared in Example 1 at a concentration of 0.14%. The mixture was stirred for 5 minutes.

The microplate was allowed to stand on a magnet-including sedimentation acceleration base for 5 minutes. The microplate was then removed from the sedimentation acceleration base and placed on a pattern reading base free from the effect of magnetic force and allowed to stand thereon at an inclination of about 45° for one minute to observe the slippage state of a coating of the sedimented particles at the bottom of each well, whereby the presence or absence of the immune reaction was judged in the same manner as in Example 5. The results were the same as in Example 3 shown in TABLE 1.

Figure 4:
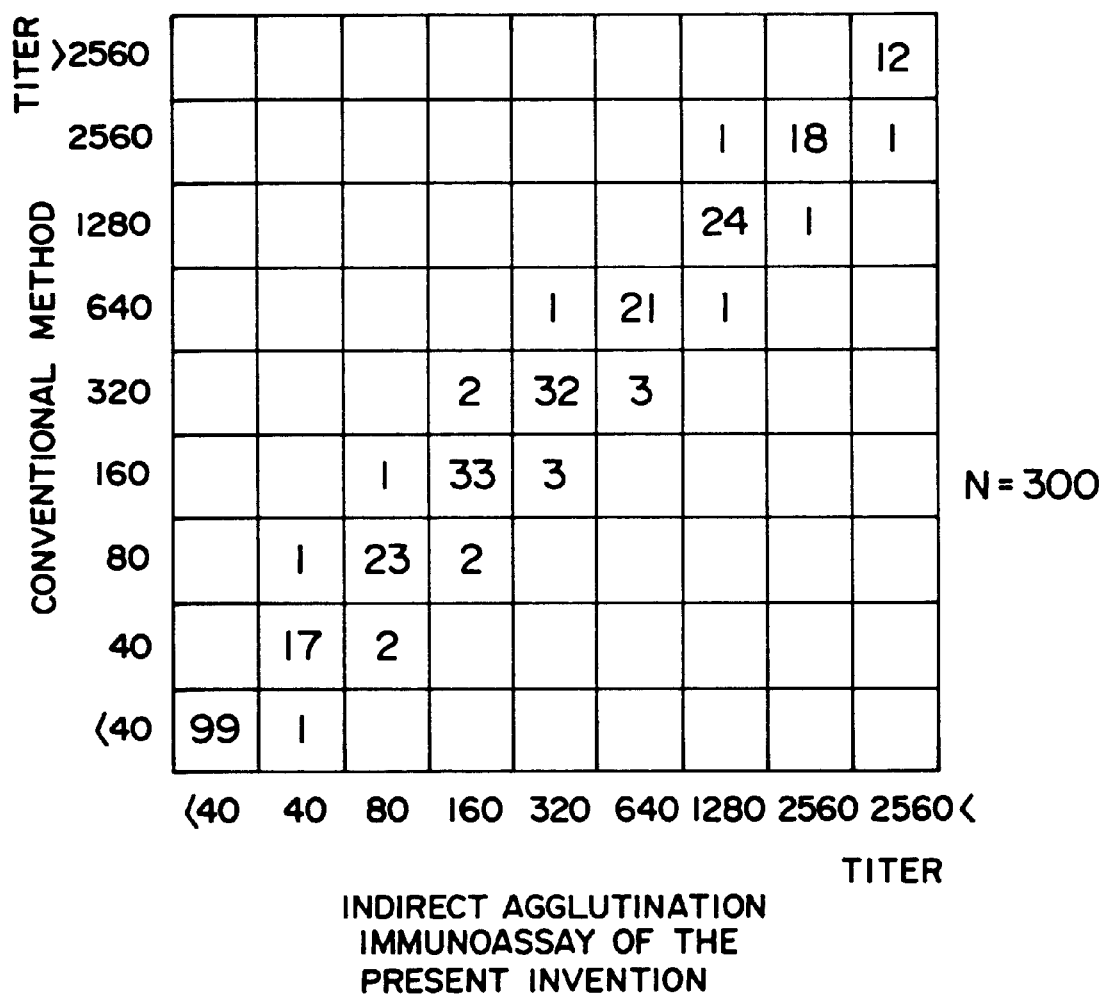

FIG. 4 shows the relationship between the above-mentioned immunoassay according to the present invention and a conventional standing method using a commercially available reagent for the detection of alpha($\alpha$)-fetoprotein (Trademark "Serodia AFP mono" made by Fujirebio Inc. with respect to the respective titers.

EXAMPLE 7

Assay of AFP in Whole Blood

A blood serum test sample containing AFP was diluted by 5 times with a blood serum dilution liquid. To this diluted blood serum test sample was added a whole blood collected from a man in good health in an amount equal to the amount of the diluted blood serum test sample, whereby a test sample was prepared.

50 $\mu$l of the thus prepared test sample was placed in a first V-shaped well of a microplate. 25 $\mu$l of the blood serum dilution liquid was placed in each of a second well through an eighth well of the microplate. 25 $\mu$l of the test sample was taken from the first well, and by use of the test sample, a $2^n$ dilution was sequentially performed from the second well through the eighth well.

To each diluted test sample placed in the V-shaped wells of the microplate was added 25 $\mu$l of a dispersion of the gelatin particles containing anti-human AFP sensitized ferricolloid prepared in Example 1 at a concentration of 0.14%. The mixture was stirred for 5 minutes.

The microplate was allowed to stand on a magnet-including sedimentation acceleration base for 5 minutes. The microplate was then removed from the sedimentation acceleration base and placed on a pattern reading base free from the effect of magnetic force and allowed to stand thereon at an inclination of about 45° for one minute to observe the slippage state of a coating of the sedimented particles at the bottom of each well, whereby the presence or absence of the immune reaction was judged in the same manner as in Example 5. The results were the same as in Example 4 shown in TABLE 1.

EXAMPLE 8

Preparation of Gelatin Particle Containing ATLV Antigen Sensitized Ferricolloid Gelatin particles containing ATLV antigen sensitized ferricolloid were prepared by application of ATLV antigen to ferricolloid-containing gelatin particles having an average particle size of about 2.5 microns disclosed in Japanese Laid-Open Patent Application 59-195161 in accordance with a conventional method disclosed in Japanese Laid-Open Patent Application 60-44870.

EXAMPLE 9

Assay of ATLV Antibody in Blood Serum

25 $\mu$l of a blood serum dilution liquid was placed in each of V-shaped wells of a microplate. 25 $\mu$l of a blood serum test sample was added to the blood serum dilution liquid in a first well. From the first well, 25 $\mu$l of the diluted blood serum test sample was taken. By use of the diluted blood test sample, a $2^n$ dilution was sequentially performed from the second well through the twelfth well. To each diluted test sample placed in the V-shaped wells of the microplate was added 25 $\mu$l of a dispersion of the gelatin particle containing the ATLV antigen sensitized ferricolloid prepared in Example 8 at a concentration of 0.2%. The mixture was stirred for 5 minutes.

The microplate was allowed to stand on a magnet-including sedimentation acceleration base for 30 seconds. The microplate was then removed from the sedimentation acceleration base and placed on a pattern reading base free from the effect of magnetic force and allowed to stand thereon at an inclination of about 60° for one minute to observe the slippage state of a coating of the sedimented particles at the bottom of each well, whereby the presence or absence of the immune reaction was judged in the same manner as in Example 5.

FIG. 5 shows the relationship between the above-mentioned immunoassay according to the present invention and a conventional standing method using a commercially available reagent for the detection of ATLV antibody (Trademark "Serodia ATLV antibody detection agent" made by Fujirebio Inc.) with respect to the respective titers.

EXAMPLE 10

Preparation of Gelatin Particle Containing HIV Antigen Sensitized Ferricolloid Gelatin particles containing HIV antigen sensitized ferricolloid were prepared by application of HIV antigen to ferricolloid-containing gelatin particles having an average particle size of about 2.5 microns disclosed in Japanese Laid-Open Patent Application 59-195161 in accordance with a conventional method disclosed in Japanese Laid-Open Patent Application 62-182662.

EXAMPLE 11

Assay of HIV Antibody in Blood Serum)

75 $\mu$l of a blood serum dilution liquid was placed in each of wells of a microplate. 25 $\mu$l of a blood serum test sample was added to the blood serum dilution liquid in a first well. From the first well, 25 $\mu$l of the diluted blood serum test sample was taken. By use of the diluted blood test sample, a $2^n$ dilution was sequentially performed from the second well through the twelfth well. To each diluted test sample placed in the V-shaped wells of the microplate was added 25 $\mu$l of a dispersion of the gelatin particle containing HIV antigen sensitized ferricolloid prepared in Example 10 at a concentration of 0.2%. The mixture was stirred for 5 minutes.

The microplate was allowed to stand on a magnet-including sedimentation acceleration base for 30 seconds. The microplate was then removed from the sedimentation acceleration base and placed on a pattern reading base and allowed to stand thereon at an inclination of about 60° for one minute to observe the slippage state of a coating of the sedimented particles at the bottom of each well, whereby the presence or absence of the immune reaction was judged in the same manner as in Example 5.

Figure 6:
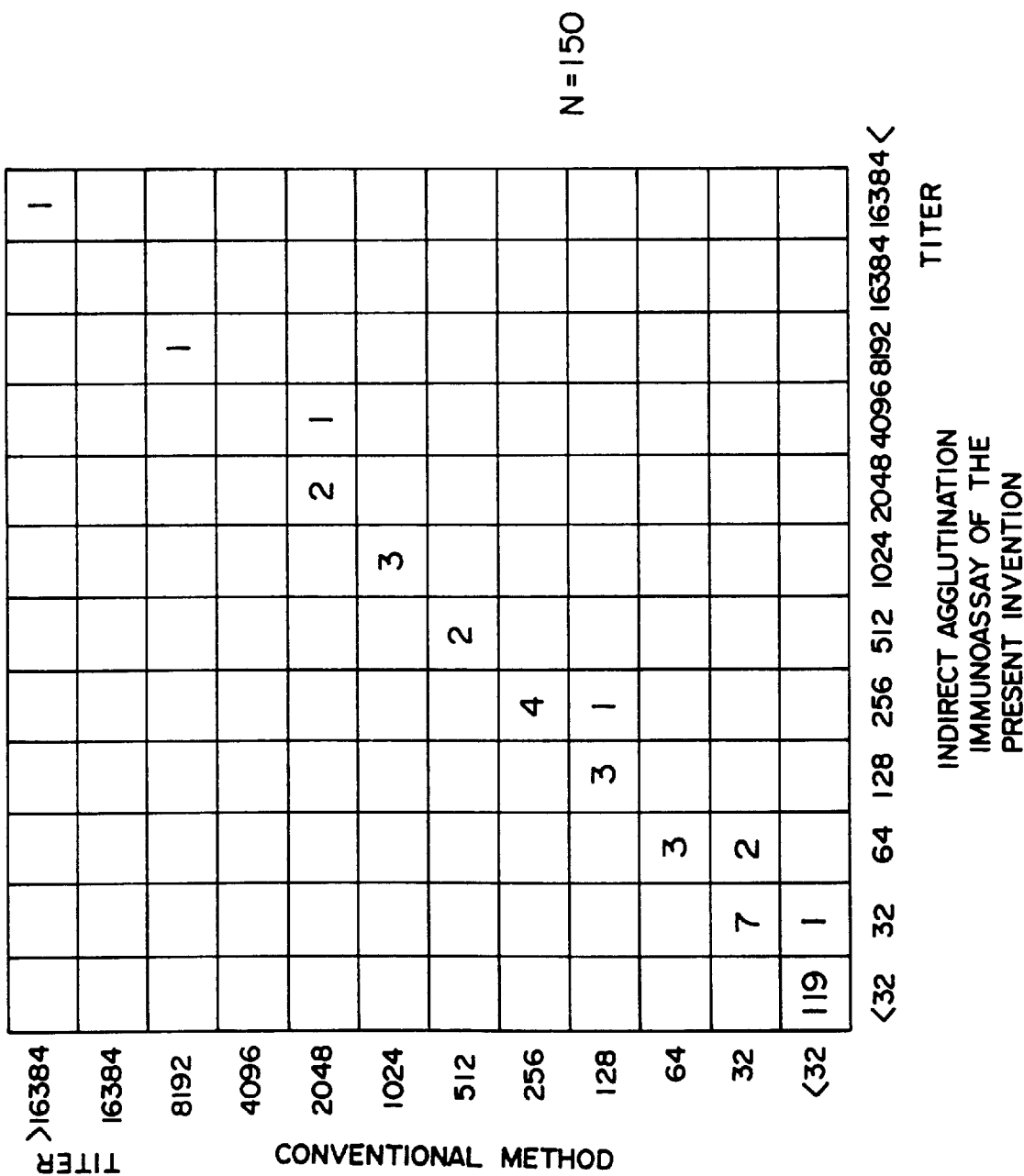

FIG. 6 shows the relationship between the above-mentioned immunoassay according to the present invention and a conventional standing method using a commercially available reagent for the detection of ATLV antibody (Trademark "Serodia ATLV antibody detection agent" made by Fujirebio Inc. with respect to the respective titers.

Thus, according to the present invention, the indirect agglutination immunoassay can be easily automized in sharp contrast to the conventional method by using a centrifuge. Furthermore, the indirect agglutination immunoassay according to the present invention can be conducted in a shorter time as compared with the conventional standing method, without being affected by environmental conditions such as vibrations. In addition, according to the present invention, whole blood can be employed as a test sample without any problems, which is impossible in the case of the conventional method using a centrifuge. Finally, there is a conspicuous correlation between the indirect agglutination immunoassay according to the present invention and the conventional standing method, and this assay can be applied not only to blood serum, urine and other body fluids, but also to whole blood, so that the conventional standing method can be sufficiently replaced by the indirect agglutination immunoassay according to the present invention and the present invention provides a simpler immunoassay method.

EXAMPLE 12

Preparation of Gelatin Particles Containing HTLV-I Antigen Sensitized Ferricolloid In accordance with Boyden Method (I. Exp. Med. 93 107–120 (1951), human T-cell leukemia virus (HTLV-I) antigen was subjected to a tannic acid treatment, so that HTLV-I was deactivated, and was absorbed by three kinds of ferricolloid-containing gelatin particles having an average particle size of 1 µm, an average particle size of 2.0 µm, and an average particle size of 2.5 µm, respectively, disclosed in Japanese Laid-Open Patent Application 59-195161, whereby three types of HTLV-I antigen-sensitized-ferricolloid containing gelatin particles were prepared.

EXAMPLE 13

Assay of HTLV-I Antibody in Blood Serum

Two test samples of blood serums were collected from two patients of T-cell leukemia, which are referred to as a first test sample and a second test sample, respectively. Further, one test sample of blood serum was collected from a well-person, which is referred to a third test sample.

25 µl of a blood serum dilution liquid was placed in each V-shaped well of a V-shaped bottom well microplate.

25 µof the first test sample was added to the 25 µl of the blood serum dilution liquid in the first V-shaped well of the microplate, so that the first test sample was diluted with 25 µl of the blood serum dilution liquid. Thus, 50 µl of a blood serum test sample diluted to ½ was placed in the first V-shaped well.

25 µl of the diluted blood serum test sample was taken from the first V-shaped well, and was added to the 25 µl of the blood serum dilution liquid in the second V-shaped well of the microplate, so that the first test sample was diluted with 25 µl of the blood serum dilution liquid. Thus, 50 µl of a blood serum test sample diluted to ¼ was placed in the second V-shaped well.

The above dilution of the first blood serum test sample with the blood serum dilution liquid was successively repeated up to the 11th V-shaped well, so that a $2^n$ dilution was carried out.

25 µl of a dispersion containing 0.25% of one of the three types of the HTLV-I antigen-sensitized-ferricolloid containing gelatin particles prepared in Example 12 was successively added to each of the 3rd to 11th V-shaped wells.

The above-mentioned procedure was repeated by replacing the first test sample, with the second and third test examples, and the HTLV-I antigen-sensitized-ferricolloid containing gelatin particles employed above by the other two types of HTLV-I antigen-sensitized-ferricolloid containing gelatin particles, respectively.

Each of the mixtures was stirred for 5 minutes. The microplate was allowed to stand still on a magnet-including sedimentation acceleration base for 1 minute. The microplate was then removed from the sedimentation acceleration base and placed on a pattern reading base free from the effect of magnetic force and allowed to stand thereon at an inclination of about 65° to observe the slippage state of a coating of the sedimented particles on the bottom of each well, whereby the presence or absence of the immune reaction was judged and the assay of the HTLV-I antibody in the blood serum of each of the above test samples was conducted.

With respect to the above-mentioned three test samples, which were diluted with the blood serum dilution liquid in the same manner in a U-shaped bottom well microplate, the assay of the HTLV-I antibody in the blood serum of each of the above test samples was conducted by a conventional standing method using a commercially available reagent for the detection of HTLV-I antibody (Trademark "Serodia HTLV-I antibody detection agent" made by Fujirebio Inc.) instead of the above employed HTLV-I antigen-sensitized-ferricolloid containing gelatin particles.

The results are shown in the following TABLE 2 and FIGS. 10 through 13:

TABLE 2

| | | Assay of HTLV-I Antibody | | | | | | | | | |
|---|---|---|---|---|---|---|---|---|---|---|---|
| Final Serum Dilution Ratio | | 1:16 | 1:32 | 1:64 | 1:128 | 1:256 | 1:512 | 1:1024 | 1:2048 | 1:4096 | Reference Medium |
| Serodia HTLV-I | 1st Sample | + | + | + | + | + | + | − | − | − | − |
| (Standing Method) | 2nd Sample | + | + | + | + | + | − | − | − | − | − |
| | 3rd Sample | − | − | − | − | − | − | − | − | − | − |
| Ferricoloid-containing | 1st Sample | + | + | + | + | + | + | − | − | − | − |
| Gelatin Particles | 2nd Sample | + | + | + | + | + | − | − | − | − | − |
| (1.5 µm) | 3rd Sample | − | − | − | − | − | − | − | − | − | − |
| Ferricoloid-containing | 1st Sample | + | + | + | + | + | + | − | − | − | − |
| Gelatin Particles | 2nd Sample | + | + | + | + | + | − | − | − | − | − |
| (2.0 µm) | 3rd Sample | − | − | − | − | − | − | − | − | − | − |

TABLE 2-continued

Assay of HTLV-I Antibody

| Final Serum Dilution Ratio | | 1:16 | 1:32 | 1:64 | 1:128 | 1:256 | 1:512 | 1:1024 | 1:2048 | 1:4096 | Reference Medium |
|---|---|---|---|---|---|---|---|---|---|---|---|
| Ferricoloid-containing | 1st Sample | + | + | + | + | + | + | − | − | − | − |
| Gelatin Particles | 2nd Sample | + | + | + | + | + | − | − | − | − | − |
| (2.5 μm) | 3rd Sample | − | − | − | − | − | − | − | − | − | − |

What is claimed is:

1. An indirect agglutination immunoassay comprsing the steps of:
   contacting, in a container, a test sample containing a desired analyte and a reagent comprising sensitized magnetic-material containing particles containing iron, wherein said sensitized magnetic-material containing particles have immobilized thereon an antigen or antibody which specifically binds to said desired analyte,
   precipitating said sensitized magnetic-material containing particles by the application of magnetic force,
   allowing said container to stand at an inclination, and
   detecting the presence or absence of an immune reaction from the absence or presence, respectively, of slippage of the precipitated sensitized magnetic-material containing particles on the bottom of said container.

2. The indirect agglutination immunoassay as claimed in claim 1, wherein said test sample is blood serum.

3. The indirect agglutination immunoassay as claimed in claim 1, wherein said test sample is whole blood.

4. The indirect agglutination immunoassay as claimed in claim 1, wherein said magnetic-material containing particles have a particle size in the range of from 2.5–3 μm.

5. An indirect agglutination immunoassay consisting essentially of the steps of:
   contacting, in a container, a test sample containing a desired analyte and a reagent comprising sensitized magnetic-material containing particles containing iron, wherein said sensitized magnetic-material containing particles have immobilized thereon an antigen or antibody which specifically binds to said desired analyte,
   precipitating said sensitized magnetic-material containing particles by the application of magnetic force,
   allowing said container to stand at an inclination, and
   detecting the presence or absence of an immune reaction from the absence or presence, respectively, of slippage of the precipitated sensitized magnetic-material containing particles on the bottom of said container.

6. The indirect agglutination immunoassay as claimed in claim 5, wherein said magnetic-material containing particles have a particle size in the range of from 2.5–3 μm.

7. The indirect agglutination immunoassay as claimed in claim 5, wherein said test sample is blood serum.

8. The indirect agglutination immunoassay as claimed in claim 5, wherein said test sample is whole blood.

9. An indirect agglutination immunoassay consisting of the steps of:
   contacting, in a container, a test sample containing a desired analyte and a reagent comprising sensitized magnetic-material containing particles containing iron, wherein said sensitized magnetic-material containing particles have immobilized thereon an antigen or antibody which specifically binds to said desired analyte,
   precipitating said sensitized magnetic-material containing particles by the application of magnetic force,
   allowing said container to stand at an inclination, and
   detecting the presence or absence of an immune reaction from the absence or presence, respectively, of slippage of the precipitated sensitized magnetic-material containing particles on the bottom of said container.

10. The indirect agglutination immunoassay as claimed in claim 9, wherein said magnetic-material containing particles have a particle size in the range of from 2.5–3 μm.

11. The indirect agglutination immunoassay as claimed in claim 9, wherein said test sample is blood serum.

12. The indirect agglutination immunoassay as claimed in claim 9, wherein said test sample is whole blood.

* * * * *